United States Patent [19]
Gammell

[11] Patent Number: 5,088,327
[45] Date of Patent: Feb. 18, 1992

[54] PHASE CANCELLATION ENHANCEMENT OF ULTRASONIC EVALUATION OF METAL-TO-ELASTOMER BONDING

[75] Inventor: Paul M. Gammell, Silver Spring, Md.

[73] Assignee: The United States of America as represented by the Secretary of the Navy, Washington, D.C.

[21] Appl. No.: 524,414

[22] Filed: May 17, 1990

[51] Int. Cl.⁵ .................................................. G01N 29/04
[52] U.S. Cl. ........................................ 73/588; 73/582
[58] Field of Search ................. 73/582, 583, 588, 579, 73/600, 602, 627

[56] References Cited

U.S. PATENT DOCUMENTS

| | | | |
|---|---|---|---|
| 3,466,652 | 9/1969 | Heyser | 367/101 |
| 3,605,486 | 8/1971 | Anderholm et al. | 73/788 |
| 4,088,028 | 5/1978 | Hildebrant | 73/611 |
| 4,100,808 | 7/1978 | Evans et al. | 73/588 |
| 4,274,288 | 6/1981 | Tittmann et al. | 73/602 |
| 4,279,019 | 7/1981 | Heyser | 364/569 |
| 4,755,953 | 7/1988 | Geithman et al. | 364/507 |
| 4,799,168 | 1/1989 | Sarr | 364/507 |
| 5,803,638 | 2/1989 | Nottingham et al. | 364/507 |

FOREIGN PATENT DOCUMENTS 61-254850 11/1986 Japan ...................................... 73/602

OTHER PUBLICATIONS

"Ultrasonic Procedures for Predicting Adhesive Bond Strength", by Joseph L. Rose et al., Mat. Eval., Jun. 1973, pp. 109–114.

Primary Examiner—Hezron E. Williams
Assistant Examiner—Louis M. Arana
Attorney, Agent, or Firm—Kenneth E. Walden; Jacob Shuster

[57] ABSTRACT

Acoustical radiation is generated and applied to the bonding interface between a radiation transmission material and a radiation attenuating material to determine adhesion quality by extraction of data from a response signal produced by echoes reflected from both the interface and the radiation entry surface on the radiation transmissive material exposed to the generated acoustical radiation. Signal phase cancellation between the echoes from the entry surface and bonding interface produce a signal signature from which the quality of bonding is evaluated. By partial attenuation of the echo from the entry surface, the signature is maximized.

17 Claims, 4 Drawing Sheets

PHASE CANCELLATION ENHANCEMENT OF ULTRASONIC EVALUATION OF METAL-TO-ELASTOMER BONDING

BACKGROUND OF THE INVENTION

This invention relates generally to the monitoring and evaluation of interface bonding between different material layers and more particularly to the determination of bonding integrity at interfaces between an acoustical radiation transmissive material such as metal and a radiation attenuating material such as an elastomer.

The concept of generating and applying pulsed radiation to bonded materials to determine adhesion integrity by measurement of response signal amplitude of reflected radiation is already known, as disclosed for example in U.S. Pat. No. 3,605,486 to Anderholm et al. According to the Anderholm et al patent, stress pressure waves induced by the pulsed radiation internally of the bonded materials partially cancel each other to affect the reflected response signal picked up for bonding evaluation. However, such evaluation involves incrementally increasing the amplitude of the stress pressure waves induced until bond failure is achieved in order to determine bond quality by measurement of the maximum signal amplitude Various signal processing techniques associated with systems for testing and evaluating ultrasonic acoustical materials are disclosed in U.S. Pat. No. 4,088,028 to Hildebrandt and U.S. Pat. Nos. 4,274,828, 4,755,953, 4,799,168 and 4,803,638. Partial signal phase cancellation and logarithmic scaling techniques are furthermore respectively referred to in U.S. Pat. Nos. 4,274,288 and 4,755,953 to Tittman et al. and Geithman et al. The technique of gating echo pulses by means of acceptance time windows is disclosed in each of U.S. Pat. Nos. 4,799,168 and 4,803638 to Sarr and Nottingham et al, respectively. However, the signal processing techniques disclosed in the latter referred to patents are not associated with the evaluation of bonding integrity.

Time delay spectrometers of the acoustical type are generally known in the art as disclosed in U.S. Pat. Nos. 3,466,652 and 4,279,019 to Heyser, as well as associated signal processing techniques. However, such spectrometer arrangements, because of time/frequency measurement limitations, are not satisfactory for use in measuring and evaluating the effects of interface bonding integrity on acoustic resonance.

It is therefore an important object of the present invention to provide a new and useful pulse echo type of material inspection system for reliably determining interface bonding integrity without destruction of the bonding so as to have widespread commercial applications as well as for critical explosive/propellant purposes in warheads and rocket motors.

SUMMARY OF THE INVENTION

In accordance with the present invention, swept frequency radiation echoes received as a response by a time delay spectrometer are utilized to nondestructively evaluate the integrity of interface bonds between a radiation transmissive metal plate and a radiation attenuating elastomer. An important aspect of the present invention resides in the reliable identification of signature signal dips in the response signals when modified by partial cancellation of the signal phase attributable to acoustical echo reflections from the front wall surface of the metal plate through which ultrasonic acoustical radiation enters along a propagation path terminated at its bonding interface with the elastomer. Measurement of amplitude and width of the signature signal dips of the modified response signals when properly tuned provides the data from which bonding integrity is determined.

BRIEF DESCRIPTION OF THE DRAWING FIGURES

Other objects, advantages and novel features of the invention will become apparent from the following detailed description of the invention when considered in conjunction with the accompanying drawing wherein.

DETAILED DESCRIPTION OF THE PREFERRED EMBODIMENTS

Figure 1:
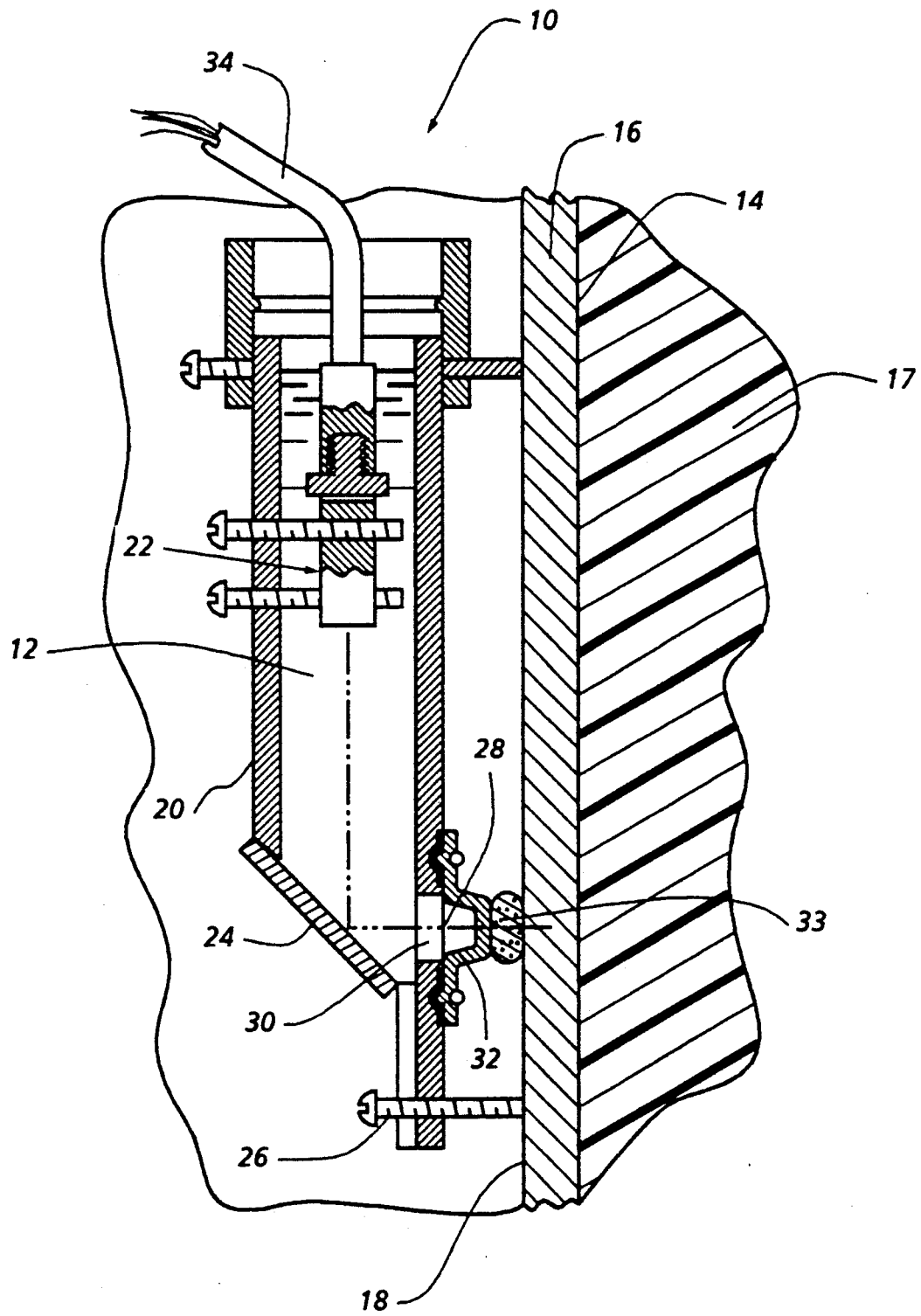
FIG. 1 is a partial side section view of a spectrometer installation in accordance with one embodiment of the present invention.

Referring now to the drawing in detail, FIG. 1 illustrates by way of example an installation of a portable ultrasonic spectrometer probe 10. The probe 10 is thereby arranged to scan the bonding interface 14 between a vertically elongated metal plate 16, which is radiation transmissive, and a radiation attenuating elastomeric material 17.

The probe 10 is adjustably mounted in close spaced relation to a front wall entry surface 18 of the metal plate 16, and includes an elongated housing 20 enclosing a body of water 12 acting as an ultrasonic coupling medium in the illustrated environment depicted in FIG. 1. A transducer 22 of the spectrometer probe 10 is mounted in an adjustably fixed position within housing 20 above an inclined acoustic mirror 24 fixed to the lower end of the housing spaced from the entry surface 18 of plate 16 by an alignment adjustment element or screw 26. Ultrasonic acoustical radiation pulses emitted from and echoes thereof received by the transducer 22 within housing 20 are reflected by the mirror 24 to establish a propagation path 28 extending through the plate 16 and terminating at the bonding interface 14 as shown. The acoustical energy is propagated along path 28 to and from the probe housing 20 through a window 30 and a sealing membrane 32 removably secured to the housing to prevent outflow of water. In a dry scanning environment as shown in FIG. 1, a coupling gel 33 is placed between the membrane 32 and the front wall surface 18. Where the front wall entry surface 18 forms an enclosure filled with water, the membrane 32 and gel 33 are not needed.

Figure 2:
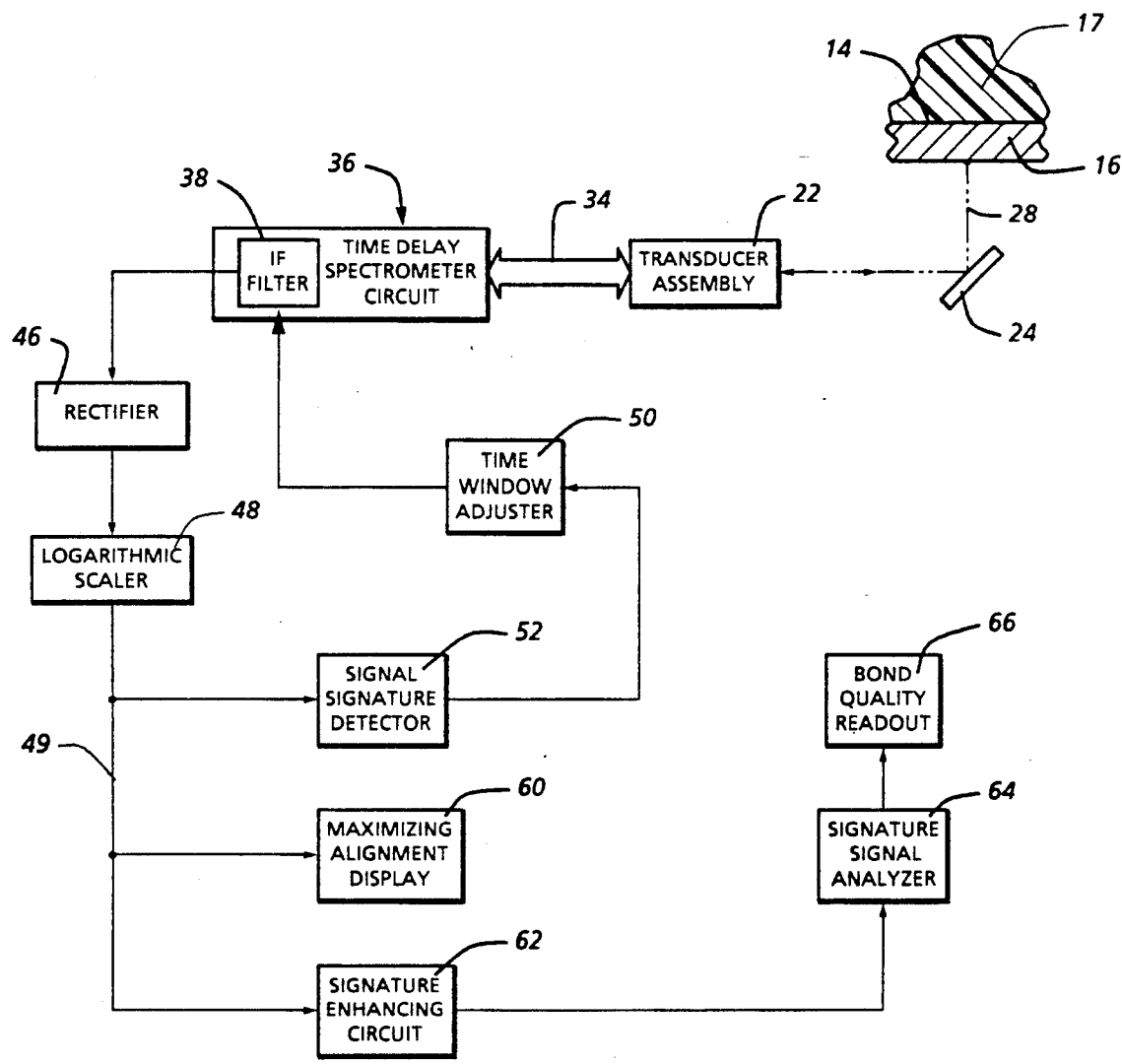
FIG. 2 is a block diagram of the signal data and processing system associated with the installation depicted in FIG. 1.

The transducer 22 of the spectrometer probe 10 as diagrammed in FIG. 2 is operatively connected through electrical cable 34 to its associated electronics in the form of time delay spectrometer circuitry 36 of a type generally known in the art as described for example in the aforementioned Heyser patents. This type of circuitry uses a swept frequency source having a moderately slow sweep rate and a receiver which follows a received echo signal through tracking filter means discriminating against signals other than those within a desired time window, and also providing narrow band, signal-to-noise enhancement. Such a tracking filter circuitry 36 utilizing heterodyne techniques, includes a fixed IF filter 38 as also diagrammed in FIG. 2 to limit the effective response to received echo signals having propagation delays within a desired time range.

Figure 3A:
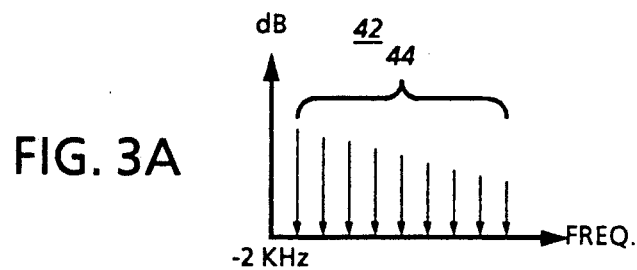
FIG. 3A is a graphical representation of the portions of the response obtained in the installation depicted in FIGS. 1 and 2.
Figure 3:
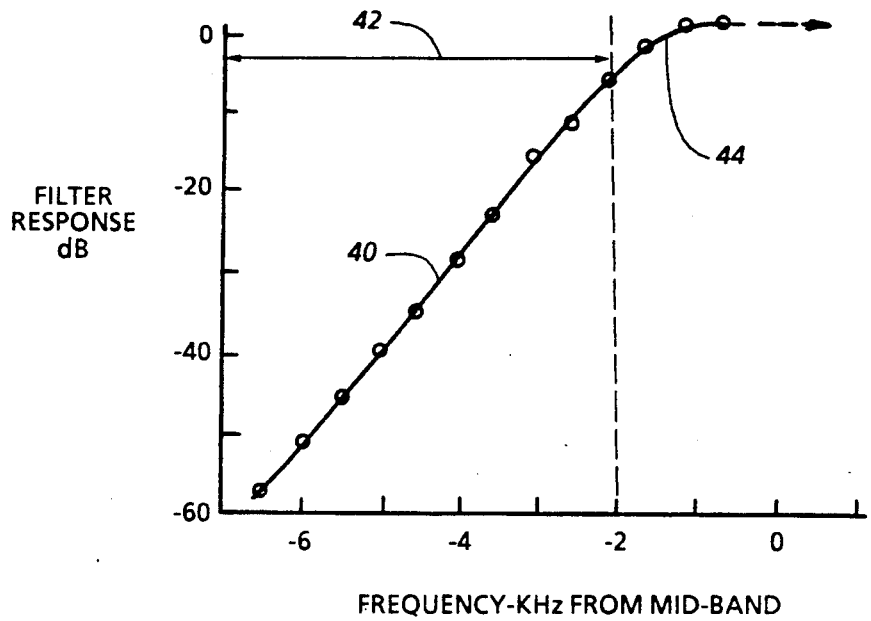
FIG. 3 is a graph of the early arrival portion of a typical spectrometer response.

FIG. 3 graphically depicts the early arrival half portion of the acoustical response 40 received by a typical time delay spectrometer. A signal frequency portion 42 of such response attributable to acoustical echoes reflected from the entry surface 18 as depicted in FIG. 3A, is reduced in accordance with the present invention by approximately the sum of the peak resonance portions 44 of the received signal attributable to acoustical echoes reflected from interface 14. Such partial attenuating of the response is achieved during the mixing action which occurs within the IF filter 38 diagrammed in FIG. 2. The modified response emerging from the filter 38 is then rectified in rectifier 46 and subjected to logarithmic scaling at 48 to emphasize the peak portions thereof.

Since the acoustic impedance of the elastomer 17 is less than that of metal plate 16 which in turn has a higher acoustic impedance than that of the body of water 12, acoustic signals reflected from front wall surface 18 and the bonding interface 14 are opposite in phase. The acoustical echoes from interface 14 are reinforced to produce peaks in the reflected signal under such conditions in which the frequencies of the input acoustical signals traveling through metal plate 16 involve an integral number of half wavelengths. Mixing of the echoes of such input signals reflected from interface 14 with the relatively frequency-independent echoes reflected from the front wall surface 18, causes the aforementioned reduction in the signal portion 42 of the response to produce cancellation dips therein. Such cancellation dips are maximized by the response modifying effect of filter 38 in approximately equalizing the amplitudes of the aforementioned signal portion 42 and sum of peak resonance portions 44. The resultant signal dips in the modified response are so maximized to produce a most clear signature of bond condition at the interface 14 in the logarithmic signal output in line 49 diagrammed in FIG. 2

As also diagrammed in FIG. 2, a time window adjuster 50 is operatively connected to the filter 38 of spectrometer circuit 36 in accordance with the present invention. The time delay of the spectrometer signal acceptance window is thereby adjusted for partial cancellation of a portion of the response attributable to acoustic reflection from the entry surface 18. Such partial cancellation effect of the acceptance window adjustment action, emphasizes the resultant signal dips in the modified response to identify signature signal characteristics with respect to which time window adjustment may be optimized through a signal signature detector 52 connected to output line 49 as diagrammed in FIG. 2.

Figure 4:
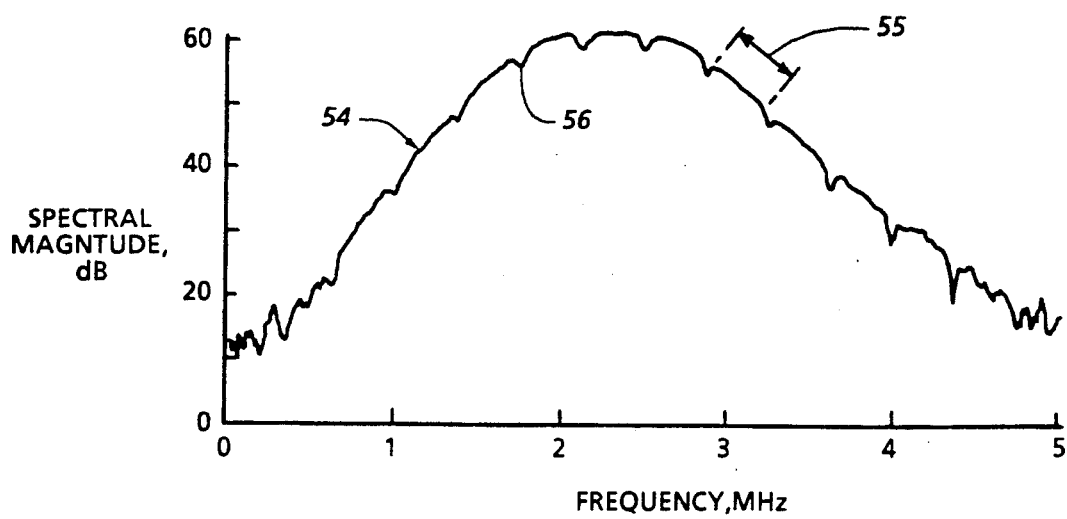
FIG. 4 is a graphical illustration of a modified response signal associated with the present invention.

FIG. 4 graphically illustrates a typical modified response signal 54 having signature signal dips including dip portion 56 located at the resonance peak portion of the modified response signal corresponding to maximum transducer response. The portion 55 of the modified response signal 54 between the dips as depicted in FIG. 4, are maximized by positionally adjusting the probe 10 through screw 26 as aforementioned so as to align the acoustical propagation path 28 normal to the entry surface 18. To assist in such adjustment, the modified response signal may be visually exhibited prior to further processing, through a maximizing alignment display 60 as diagrammed in FIG. 2. Assistance for alignment and flaw identification may thereby be provided.

The signature signal dip portion 56 of the modified response signal 54 as depicted in FIG. 4, may be made more pronounced by differentiation or high pass filtering processes through a signature enhancing circuit 62 as diagrammed in FIG. 2. An expanded maxima portion of the modified response signal with the pronounced signature signal dip is thereby fed to a signature signal analyzer 64 through which bonding quality data is extracted and made available through readout 66 as diagrammed in FIG. 2 in accordance with well known signal processing techniques.

Figure 5A:
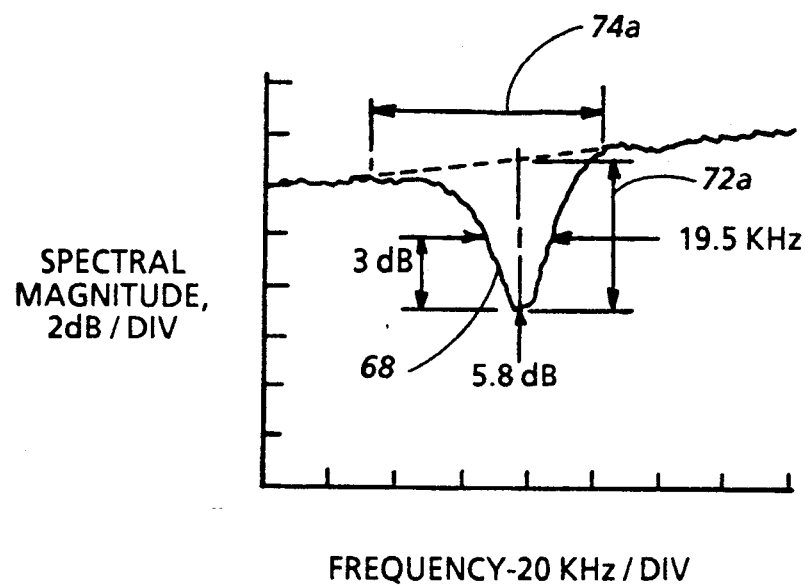
FIGS. 5A and 5B are graphical illustrations of optimized resonance peak portions of modified response signals having signature signal dips respectively characterizing bonded and unbounded interfaces being evaluated by the system of the present invention.
Figure 5B:
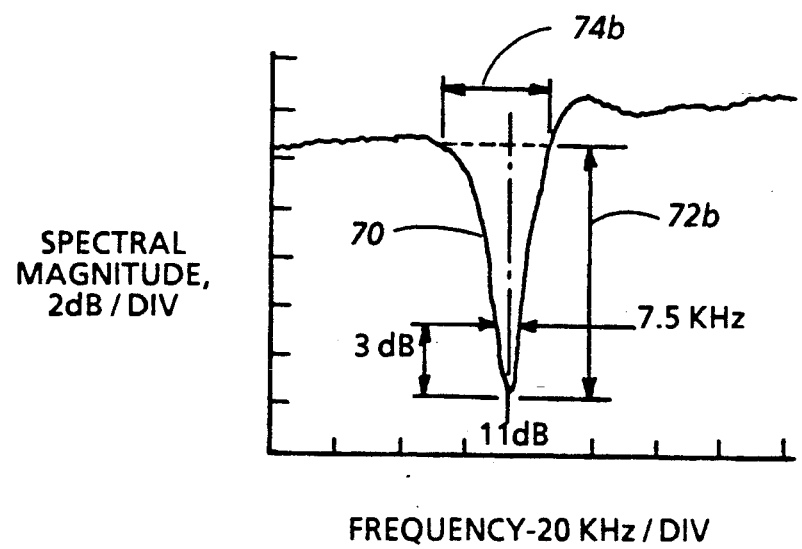

FIGS. 5A and 5B depict the expanded and pronounced signature portion of modified response signals produced in accordance with the present invention, respectively exhibiting signature dips 68 and 70 for bonded and unbonded interfaces. It will be observed that the signature dip 68 for the bonded interface is characterized by amplitude 72a and width 74a that are respectively less than and greater than the amplitude 72b and width 74b of the signature dip 70 reflecting the unbonded interface. Accordingly, adhesion or bonding integrity is quantitized by the analyzer 64 as an inverse function of signature dip amplitude 72 and a direct function of signature dip width 74.

As a result of the foregoing described material inspection system, the integrity of a metal-to-elastomer bond may be assessed in a non-destructive and reliable manner, particularly critical in solid rocket motors. The described system will also be useful for inspection of other critical and safety related structures involving interface bonds, including but not limited to vibration damping mechanisms.

Numerous modifications and variations of the present invention are possible in light of the foregoing teachings. It is therefore to be understood that within the scope of the appended claims the invention may be practiced otherwise than as specifically described.

What is claimed is:

1. In a system for inspection of a bonding interface between a radiation transmissive material and another material, involving emission of radiation conducted along a path through the transmissive material from an entry surface thereon and reception of echoes of the emitted radiation reflected along said path from the entry surface and the bonding interface to produce a response; a method of monitoring adhesion between said materials at the bonding interface, including the steps of:

modifying said response by partial attenuation of a portion thereof resulting from said reception of the echoes of the emitted radiation reflected from only the entry surface; maximizing a resonance peak portion of the modified response to identify a signature signal characteristic quantitized with respect to amplitude and width; and determining integrity of said adhesion at the bonding interface as an inverse function of the quantitized amplitude and a direct function of the quantitized width of said identified signature signal characteristic.

2. The method of claim 1 wherein said signature signal characteristic is a dip in the modified response at the maximized resonance peak portion thereof.

3. The method of claim 2 wherein said step of modifying the response includes: establishing a time window to which said reception of the reflected radiation is limited; and adjustably delaying establishment of the time window to embrace the signature signal characteristic at the maximized resonance peak portion of the response.

4. The method of claim 3 wherein the resonance peak portion of the response signal is maximized by aligning said path of the radiation normal to the entry surface.

5. The method of claim 4 wherein said radiation is ultrasonic energy.

6. The method of claim 5 wherein said radiation transmissive material is metal and the other material is a radiation attenuating elastomer.

7. The method of claim 1 wherein said step of: modifying the response includes: establishing a time window to which said reception of the reflected radiation is limited; and adjustably delaying establishment of the time window to embrace the signature signal characteristic at the maximized resonance peak portion of the response.

8. The method of claim 1 wherein the resonance peak portion of the response signal is maximized by aligning said path of the radiation normal to the entry surface.

9. The methods of claim 8 wherein said signature signal characteristic is a dip in the modified response at the maximized resonance peak portion thereof.

10. In combination with time delay spectrometer means for emitting radiation conducted through a radiation transmissive material between an entry surface thereof and an interface with another material, a system for monitoring bonding between said materials at the interface, including means for establishing a path, terminated at the interface, along which the emitted radiation is conducted, means responsive to reception of the emitted radiation reflected from the interface and the entry surface along said path for producing a response signal, means for modifying the response signal by partial attenuation of a portion thereof produced by the radiation reflected only from the entry surface, means maximizing a resonance peak portion of the modified response signal for identifying a signal characteristic as a signature of said bonding between the materials at the itnerface, means for quantitizing said identified signal characteristic and signal data processing means for extracting bonding quality data from the maximized resonance peak portion of the modified response signal as functions of the quantitized signal characteristic.

11. The combination of claim 10 wherein said radiation transmissive material is a metallic layer between the entry surface and the interface, said other material being a radiation attenuating elastomer.

12. The combination of claim 11 wherein said response signal modifying means includes adjusting means operatively connected to the spectrometer means for limiting said reception of the reflected radiation to a maximum response portion from which the radiation reflected from the entry surface is partially excluded.

13. The combination of claim 12 wherein said identified signature signal characteristic is a pronounced dip in the maximized resonance peak portion of the modified response signal.

14. The combination of claim 10 wherein said response signal modifying means includes adjusting means operatively connected to the spectrometer means for limiting said reception of the reflected radiation to a maximum response portion from which the radiation reflected from the entry surface is partially excluded.

15. In combination with time delay spectrometer means for emitting radiation conducted through a radiation transmissive material between an entry surface thereof and an interface with another material, a system for monitoring bonding between said materials at the interface, including means responsive to reception of the radiation reflected from the interface and the entry surface for producing a response signal, means for modifying the response signal to identify a signature signal characteristic therein, and signal data processing means for extracting bonding quality data from the modified response signal as functions of amplitude and width of said identified signature signal characteristic.

16. In a system for inspection of a bonding interface between a radiation transmissive material and another material, involving emission of radiation and reception of echoes of the emitted radiation reflected from the bonding interface to produce a response signal; a method of monitoring adhesion between said materials at the bonding interface, including the steps of: conducting the emitted radiation and the echoes along a path through the transmissive material terminated at the interface; modifying said response signal to identify a signal characteristic therein as a signature of said adhesion between said materials and evaluating quality of said adhesion at the bonding interface by quantification of the identified signal characteristic of the modified response signal.

17. In a system for inspection of a bonding interface between a radiation transmissive material and another material, involving emission of radiation conducted through the transmissive material from an entry surface thereon and reception of echoes of the emitted radiation reflected from the entry surface and the bonding interface to produce a response signal; a method of monitoring adhesion between said materials at the bonding interface, including the steps of: modifying said response signal to identify a signature signal characteristic therein;

quantitizing the identified signature signal characteristic in terms of amplitude and width; and determining different functions of said amplitude and said width of the quantized signature signal characteristic to evaluate quality of said adhesion at the bonding interface.

* * * * *